(12) United States Patent
Cartledge et al.

(10) Patent No.: US 9,975,660 B2
(45) Date of Patent: May 22, 2018

(54) CONTAINER AND DISPENSING DEVICE

(71) Applicant: HANDIPOD LIMITED, Cowbridge (GB)

(72) Inventors: Philip Vincent Cartledge, South Glamorgan (GB); Neil Paul Taylor, Dana Point, CA (US)

(73) Assignee: Handipod Limited, Cowbridge, South Glamorgan (GB)

( * ) Notice: Subject to any disclaimer, the term of this patent is extended or adjusted under 35 U.S.C. 154(b) by 0 days. days.

(21) Appl. No.: 15/519,083

(22) PCT Filed: Oct. 9, 2015

(86) PCT No.: PCT/GB2015/052964
§ 371 (c)(1),
(2) Date: Apr. 13, 2017

(87) PCT Pub. No.: WO2016/059379
PCT Pub. Date: Apr. 21, 2016

(65) Prior Publication Data
US 2017/0233136 A1    Aug. 17, 2017

(30) Foreign Application Priority Data
Oct. 13, 2014    (GB) .................................. 1418040.0

(51) Int. Cl.
*B65D 35/54*    (2006.01)
*B65D 35/28*    (2006.01)
(Continued)

(52) U.S. Cl.
CPC .......... *B65D 21/0228* (2013.01); *A45F 5/021* (2013.01); *A47K 5/1201* (2013.01);
(Continued)

(58) Field of Classification Search
CPC ........ B65D 21/028; B65D 25/28; A45F 5/021
USPC .............................. 222/93, 94, 96, 106, 192
See application file for complete search history.

(56) References Cited

U.S. PATENT DOCUMENTS 4,901,889 A * 2/1990 Mitchell ................ A47K 10/32
                                                        222/153.11
4,927,284 A * 5/1990 Tsai ..................... G02C 13/006
                                                        15/214
(Continued)

FOREIGN PATENT DOCUMENTS

DE    37 44 438 A    7/1989
DE    94 18 395 U1    1/1995
(Continued)

Primary Examiner — Vishal Pancholi
(74) Attorney, Agent, or Firm — Edwin D. Schindler

(57) ABSTRACT

A dispensing device includes first and second cylindrical portions which are detachably interconnected end-to-end. The first portion is arranged to store consumables, such as bags, for collecting pet faeces and includes a tubular sidewall 110 having an aperture formed therein through which the consumables can be dispensed. The second portion is arranged to store a fluid such as a hand sanitizer and has an outlet at one end through which the fluid can be dispensed. The dispensing device provides a convenient manner for storing consumables and associated fluids together, so that, for example, a user can sanitize their hands after picking up pet faeces using a dispensed bag.

8 Claims, 1 Drawing Sheet

(51) Int. Cl.
   *B65D 35/22*   (2006.01)
   *B65D 21/02*   (2006.01)
   *A61F 6/00*    (2006.01)
   *B65D 83/08*   (2006.01)
   *E01H 1/12*    (2006.01)
   *A47K 5/12*    (2006.01)
   *A45F 5/02*    (2006.01)
   *A61L 2/00*    (2006.01)
   *B65D 25/28*   (2006.01)
   *B65D 47/20*   (2006.01)
   *A47K 10/38*   (2006.01)

(52) U.S. Cl.
   CPC .......... *A61F 6/005* (2013.01); *A61L 2/0088* (2013.01); *B65D 25/28* (2013.01); *B65D 47/2031* (2013.01); *B65D 83/08* (2013.01); *B65D 83/0805* (2013.01); *E01H 1/1206* (2013.01); *A47K 10/3809* (2013.01); *A61L 2202/15* (2013.01); *E01H 2001/128* (2013.01)

(56) References Cited

U.S. PATENT DOCUMENTS

| | | | |
|---|---|---|---|
| 5,024,546 A * | 6/1991 | Guzman | A45D 40/262 401/16 |
| 6,076,717 A | 6/2000 | Edwards | |
| 6,321,937 B1 * | 11/2001 | DeSimone | A47K 10/3818 221/45 |
| 6,528,766 B1 * | 3/2003 | Parks | A47J 36/2433 126/261 |
| 6,883,989 B2 * | 4/2005 | Kushner | A63B 47/04 206/226 |
| 6,918,513 B1 * | 7/2005 | Downey | A47K 10/32 222/192 |
| 7,585,125 B2 * | 9/2009 | Muhlhausen | B65D 23/12 401/123 |
| 8,602,257 B2 * | 12/2013 | Godsell | B60N 3/101 206/225 |
| 2006/0011660 A1 * | 1/2006 | Sandlin | B05B 11/0013 222/321.9 |
| 2010/0116857 A1 | 5/2010 | Vickers | |
| 2010/0301136 A1 | 12/2010 | Scott | |
| 2012/0085674 A1 | 4/2012 | Kemper | |
| 2012/0152771 A1 | 6/2012 | Garside | |
| 2014/0091086 A1 | 4/2014 | Sorensen | |

FOREIGN PATENT DOCUMENTS

| | | |
|---|---|---|
| GB | 2327661 A | 2/1999 |
| WO | WO 00/15030 A1 | 3/2000 |

* cited by examiner

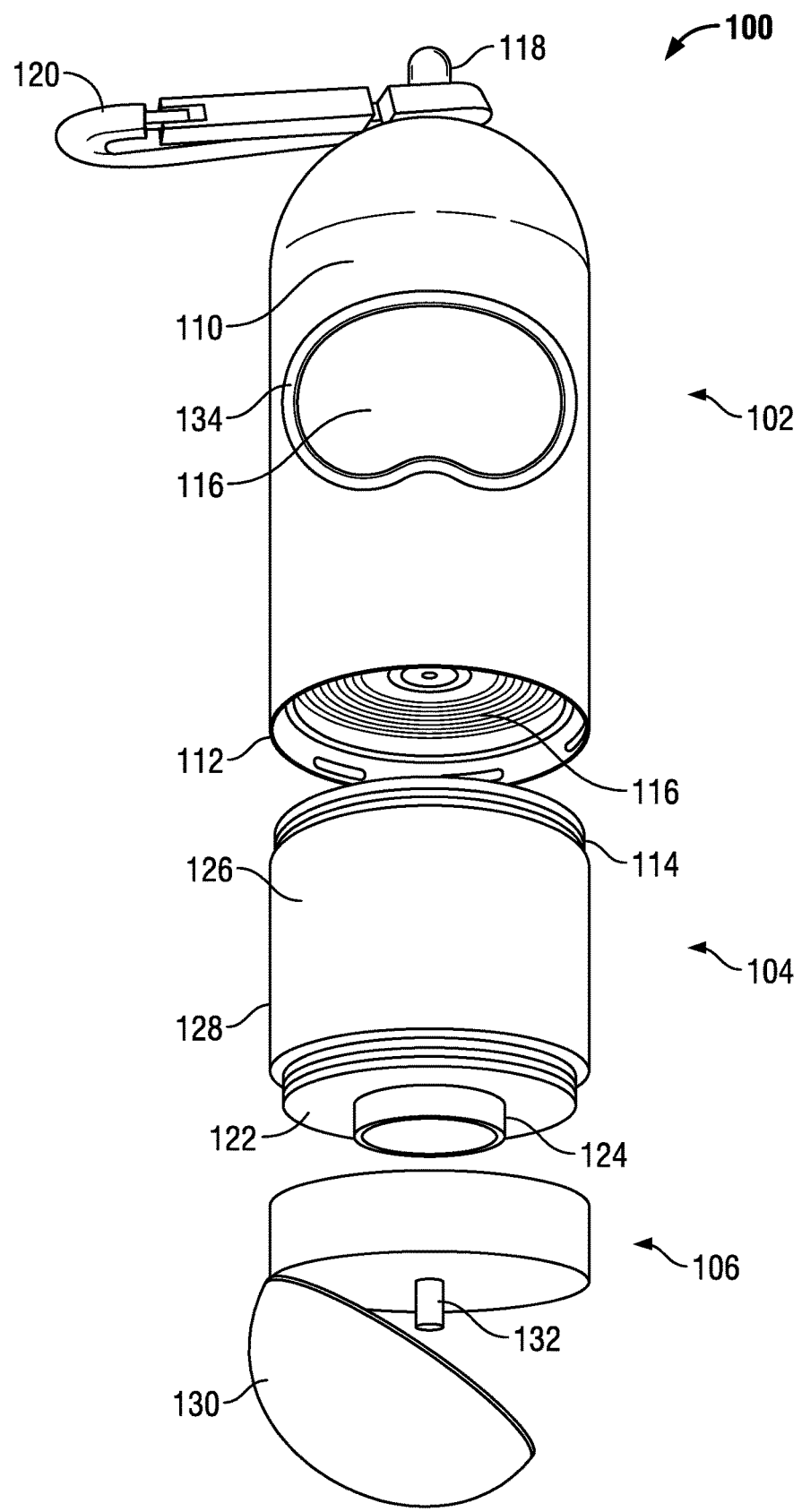

CONTAINER AND DISPENSING DEVICE

FIELD

The present invention relates to a container. Particularly, but not exclusively, the present invention relates to a container to be used as a dispensing device.

BACKGROUND

Frequently, individuals feel the need to clean their hands to remove lasting bacteria in order to mitigate against the possibility of infection due to such bacteria. Situations where an individual may seek to clean their hands include cleaning up after a pet, changing an infant's nappy and dealing with material which may be carrying such bacteria.

Aspects and embodiments were devised with the foregoing in mind.

SUMMARY

Viewed from a first aspect, there is provided a container comprising first and second portions, each portion comprising a tubular side wall having first end and a second end, the first end being closed by an end wall, the second end being adapted to detachably engage the second end of the other portion, said first portion being arranged to store a consumable and the second portion comprising a vessel being arranged to store a fluid, wherein an aperture is formed in the tubular side wall of the first portion through which the consumable can be dispensed from the first portion and further wherein the tubular side wall of the second comprises at least a deformable region arranged to deform responsive to pressure to enable the fluid to be dispensed through an outlet in the second portion, the end wall of the second portion forming a detachable closure for said outlet, the second end of the tubular side wall of the first portion being open to permit said consumable to be inserted into the first portion.

The container may be used in a dispensing device where the fluid comprises a sanitising fluid and the consumable comprises a plurality of consumables, which may be arranged on a roll, the axis of which may extend co-axially with the longitudinal axis of a side wall, which may be a tubular side wall, of the first portion.

The consumable may comprise a plurality of bags but may also comprise a plurality of other consumables such as a prophylactic or a sanitary wipe.

A container in accordance with the first aspect provides the means for carrying a consumable, such as a plastic bag that can be used to remove fecal matter deposited by a pet or a tissue that may be used during the changing of an infant's nappy, and a fluid, which may be a detergent or antibacterial solution that may be used to clean any extraneous matter left after removing fecal matter or changing an infant's nappy, together and offers a convenient means by which such a fluid may be applied quickly after the completion of such a task. Expediting the application of this fluid reduces the chances that infection will be spread by any bacteria that is present.

The first and second portions of containers in accordance with the first aspect are detachably engaged using, for example, a snap-fit connection or a screw-threaded connection. The detachable engagement of the first and second portions enables the consumable and the fluid to be easily and convenient refilled.

The second part of a container in accordance with the first aspect comprises a vessel having a deformable wall region which can be deformed to dispense the fluid through the outlet in the second portion: this provides assistance to a user when the fluid is being dispensed which means it is dispensed more quickly and in a more controlled fashion.

The deformable region is arranged to deform responsive to pressure to enable the fluid to be dispensed through the outlet in the second portion. The effect of the deformable region is that the second part is simple and cheap to manufacture, has a more streamlined profile and enables a high level of control to be taken when the fluid is being dispensed. The vessel may be entirely formed of a deformable material which reduces the demands on how dextrous a user needs to be to dispense fluid from the second portion as any part of the vessel may be used to actuate the dispensing means rather than just a specific part of the vessel.

The second portion of a container in accordance with the first aspect may further comprise an opening through which the second portion can be filled with the fluid to be dispensed.

The consumable and the fluid are contained within the container unless either of the consumable or the fluid is being refilled.

The tubular side wall may be cylindrical which makes the container more ergonomic and easier to handle and store.

The end wall of the first or second portion may be dome shaped.

The end wall of the second portion may comprise a detachable closure which closes the outlet. This inhibits the flow of the fluid from the second portion and also minimises the flow of air to the outlet which reduces the growth of bacteria in the vicinity of the outlet.

The end wall of the second portion may be provided on a detachable member which comprises the outlet for the dispensing of the fluid and which is arranged to close the opening.

The second end of the tubular side wall of the first portion is open to permit the consumable or fluid to be inserted into the respective first or second portion.

Viewed from a second aspect, there is provided a dispensing device comprising a container as hereinbefore described, a consumable contained within the first portion and a fluid contained within the second portion.

The fluid may comprise a sanitising fluid.

The consumable may comprise a plurality of consumables, which may be arranged as a roll. The axis of the roll may extend generally co-axially with the longitudinal axis of the tubular side wall of the first portion of the container.

The consumable may comprise a plurality of bags.

DESCRIPTION

An embodiment of the present invention will now be described by way of example, the single FIG. of which is an exploded view of a container according to an embodiment of the present invention.

A container 100 as illustrated with reference to FIG. 1 comprises an upper cylindrical portion 102 and a lower cylindrical portion 104.

The upper cylindrical portion 102 comprises upper 110 and lower ends 112. The upper end 110 is generally dome shaped. The lower end 112 is open and comprises a plurality of internal channels which extend circumferentially and are formed to engage a complementary external rib which extends circumferentially of an upper end 114 of the lower cylindrical portion 104 to bring the upper and lower cylindrical portions into detachable engagement using the snap-fit mechanism. The upper cylindrical portion 102 further comprises an aperture 134 formed in a side wall thereof through which a rolled consumable 116 may be dispensed. The longitiduinal axis of the rolled consumable 116 may be co-axial with the longitudinal axis of the upper cylindrical portion 102.

A loop 118 may also provided on the first part for connection of the first part 102 to a belt hook 120 or carrying strap.

The lower cylindrical portion 104 comprises a vessel 128 containing a sanitising fluid to be dispensed through an outlet 124 disposed on the lower end 122 thereof. The lower end 122 of the vessel 128 is attached to a dispensing portion 106 of the lower cylindrical portion 104. The vessel 128 comprises a deformable side wall 126 which may be deformed to apply a force to the sanitising fluid contained therein which causes the sanitising fluid to flow through the outlet 124.

The outlet 124 also provides means by which the fluid contained inside the vessel 128 can be refilled by a user if the amount of fluid inside the vessel 128 is exhausted.

The dispensing portion 106 comprises a closure 130 which can be pivoted between an open and closed position. The closure 130 is shown in FIG. 1 in its open position. The dispensing portion 106 comprises a dispensing nozzle 132 which is aligned with the outlet 124. This enables the sanitising fluid, when the side wall 126 of the vessel 128 is deformed, to flow through the outlet 124 and into the nozzle 132. If the closure 130 is in its open position then the sanitising fluid will flow through the nozzle and out of the container 100. If the closure 130 is in its closed position then a seal is formed which prevents the flow of sanitising fluid from the vessel 128 to the exterior of the container 100.

The nozzle 132 is substantially narrower than the outlet 124 to enable more control to be exerted over the flow of the sanitising fluid that is flowing through the outlet into the nozzle 132.

The dispensing portion 106 comprises a series of moulded channels or a thread (not shown) formed to engage a complementary formation (not shown) the lower cylindrical portion 104 to bring the dispensing portion 106 and the lower cylindrical portion 104 into detachable engagement. The detachable engagement of the dispensing portion 106 and the lower cylindrical portion 104 allows the dispensing portion 106 to be removed so that the vessel 128 can be refilled with sanitising fluid through the outlet 124. Optionally, the dispensing portion 106 may be integrally formed with the lower cylindrical portion 104 and a further closure (not shown) may be provided at an upper end of the vessel 128 through which the vessel 128 may be refilled with sanitising fluid.

We will now describe the use of the container 100 considering an example where the container 100 is used to sanitise a user's hands after they clean up fecal matter deposited by their pet dog.

After the fecal matter is deposited, the user can take a consumable 116, such as a plastic bag, from the plurality of plastic bags kept in the upper cylindrical portion 102 through aperture 134. The user then uses the plastic bag to pick up the fecal matter, preferably taking care not to expose themselves directly to the fecal matter. The plastic bag can then be placed into a waste disposal bin and the user then moves the closure 130 to an open position and squeezes the side wall of vessel 128 to force sanitising fluid from the vessel 128 into the hand of the user and uses the sanitising fluid to clean their hands to mitigate against the possibility of infection of any bacteria which was transferred to their hand when they used the plastic bag to dispose of the fecal matter.

Following repeated usage, either the consumable 116 kept in the upper cylindrical portion 102 or the sanitising fluid stored in the lower cylindrical portion 104 may become exhausted and require replenishment.

If the consumable 116 is exhausted, the upper cylindrical portion 102 may be detached from the lower cylindrical portion 104 and a new roll of rolled consumable 116 may be inserted into the upper cylindrical portion 102 to replenish the consumable 116.

If the sanitising fluid is exhausted, the upper cylindrical portion 102 may be detached from the lower cylindrical portion 104 and the user may either dispose of the lower cylindrical portion 104 and fit another or refill the sanitising fluid through the outlet 124.

A container in accordance with the present invention is simple and inexpensive in construction yet provides a convenient way of storing consumables and associated fluids together in a convenient manner.

The invention claimed is:

1. A dispensing device comprising a container containing a roll of consumables and a fluid, said container comprising:
    a first portion and second portion each comprising a tubular side wall having a first end and a second end, the first end of each of said first portion and said second portion being closed by an end wall, and the second end of each of said first portion and said second portion being detachably for engaging the second end of said second portion and said first portion, respectively; and,
    said roll of consumables being contained in said first portion with an axis of said roll of consumables extending substantially coaxially with a longitudinal axis of the tubular side wall of said first portion, said tubular side wall of said first portion having an aperture through which consumables are able to be dispensed from said first portion, said second portion further comprising a vessel in which the fluid is contained, said tubular side wall of said second portion comprising a deformable region deformable in response to pressure for causing the fluid to be dispensed through an outlet in said second portion, the first end wall of said second portion forming a detachable closure for the outlet, the second end of said first portion being open for permitting said roll of consumable to be inserted axially into the said first portion when said first portion and said second portion are disengaged, said second portion further comprising an opening through which the vessel is able to be filled with the fluid to be dispensed, the detachable closure and the outlet being on a detachable member for closing the opening.

2. The dispensing device according to claim 1, wherein the fluid comprises a sanitizing fluid.

3. The dispensing device according to claim 1, wherein the consumable comprises a plurality of bags.

4. The dispensing device according to claim 1, wherein said tubular side wall of each of said first portion and said second portion is cylindrical.

5. The dispensing device according to claim 1, wherein said end wall of each of said first portion and said second portion is dome-shaped.

6. The dispensing device according to claim 1, wherein said second end of the tubular side wall of said second portion is closed for containing the fluid in said second portion.

7. The dispensing device according to claim 1, wherein said first portion is detachably engageable with a portion of said second portion via a snap-fit connection.

8. The dispensing device according to claim 1, wherein said first portion is detachably engageable with a portion of said second portion via a screw-threaded connection.

* * * * *